(12) United States Patent
Lauritzen et al.

(10) Patent No.: US 9,856,228 B2
(45) Date of Patent: Jan. 2, 2018

(54) PEPTIDYL NITRIL COMPOUNDS AS DIPEPTIDYL PEPTIDASE I INHIBITORS

(71) Applicant: Prozymex A/S, Horsholm (DK)

(72) Inventors: Conni Lauritzen, Rodovre (DK); John Pedersen, Niva (DK)

(73) Assignee: PROZYMEX A/S, Horsholm (DK)

( * ) Notice: Subject to any disclaimer, the term of this patent is extended or adjusted under 35 U.S.C. 154(b) by 0 days.

(21) Appl. No.: 14/917,147

(22) PCT Filed: Sep. 8, 2014

(86) PCT No.: PCT/EP2014/069088
§ 371 (c)(1),
(2) Date: Mar. 7, 2016

(87) PCT Pub. No.: WO2015/032945
PCT Pub. Date: Mar. 12, 2015

(65) Prior Publication Data
US 2016/0207900 A1    Jul. 21, 2016

(30) Foreign Application Priority Data

Sep. 9, 2013 (EP) .................................... 13183519
Jan. 21, 2014 (EP) .................................... 14151979

(51) Int. Cl.
*A61K 31/497* (2006.01)
*C07D 309/14* (2006.01)

(52) U.S. Cl.
CPC ................... *C07D 309/14* (2013.01)

(58) Field of Classification Search
USPC ........................ 514/252.1; 544/336
See application file for complete search history.

(56) References Cited

FOREIGN PATENT DOCUMENTS

| WO | WO 2009/0784829 A1 | 6/2009 |
|---|---|---|
| WO | WO 2010/128324 A1 | 11/2010 |
| WO | WO 2010/142985 A1 | 12/2010 |
| WO | WO 2011/154677 A1 | 12/2011 |
| WO | WO 2012/119941 A1 | 9/2012 |
| WO | WO 2012/130299 A1 | 10/2012 |
| WO | WO 2013/041497 A1 | 3/2013 |
| WO | WO 2015/032945 A1 | 3/2015 |

OTHER PUBLICATIONS

Adkison, A., et al., "Dipeptidyl peptidase I activates neutrophil-derived serine proteases and regulates the development of acute experimental arthiritis," *J. Clin. Invest*, 2002, vol. 109, pp. 363-271.
Bondebjerg, J., et al., "Depeptidyl nitriles as human dipeptidyl peptidase I inhibitors," *Bioorganic & Medicinal Chemistry Letters*, 2006, vol. 16, pp. 3614-3617.
Pham, et al., "Papillon-Lefèvre Syndrome: Correlating the Molecular, Cellular, and Clinical Consequences of Cathepsin C/Dipeptidyl Peptidase I Deficiency in Humans," *The Journal of Immunology*, 2004, vol. 173(12), pp. 7277-7281.
Robichaud, J., et al., "A Novel Class of Nonpeptidic Biaryl Inhibitors of Human Cathepsin K," *J. Med. Chem.*, 2003, vol. 46(17), pp. 3709-3327.
Yang, Y., et al., "Research Progress of Depeptidyl Peptidase I," *Chinese Journal of Clinical Pharmacology and Therapeutics*, 2006, vol. 11(6), pp. 601-605.
Zeng, G., et al., "Cathepsins: Structures, Functions and Inhibitors," *Acta Botanica Yunnanica*, 2005, vol. 27(4), pp. 337-354.

*Primary Examiner* — Rei-Tsang Shiao
(74) *Attorney, Agent, or Firm* — Womble Bond Dickinson (US) LLP

(57) ABSTRACT

The invention relates to compounds of Formula (I) and their use as selective dipeptidyl peptidase I inhibitors, as well as pharmaceutical compositions comprising said compounds, and methods of treatment involving said compounds.

(I)

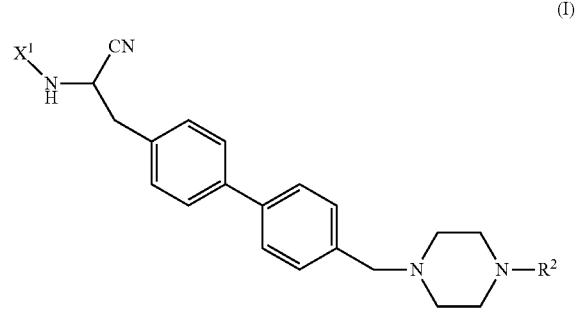

16 Claims, 4 Drawing Sheets

PEPTIDYL NITRIL COMPOUNDS AS DIPEPTIDYL PEPTIDASE I INHIBITORS

CROSS-REFERENCE TO RELATED APPLICATIONS

Figure 1A:
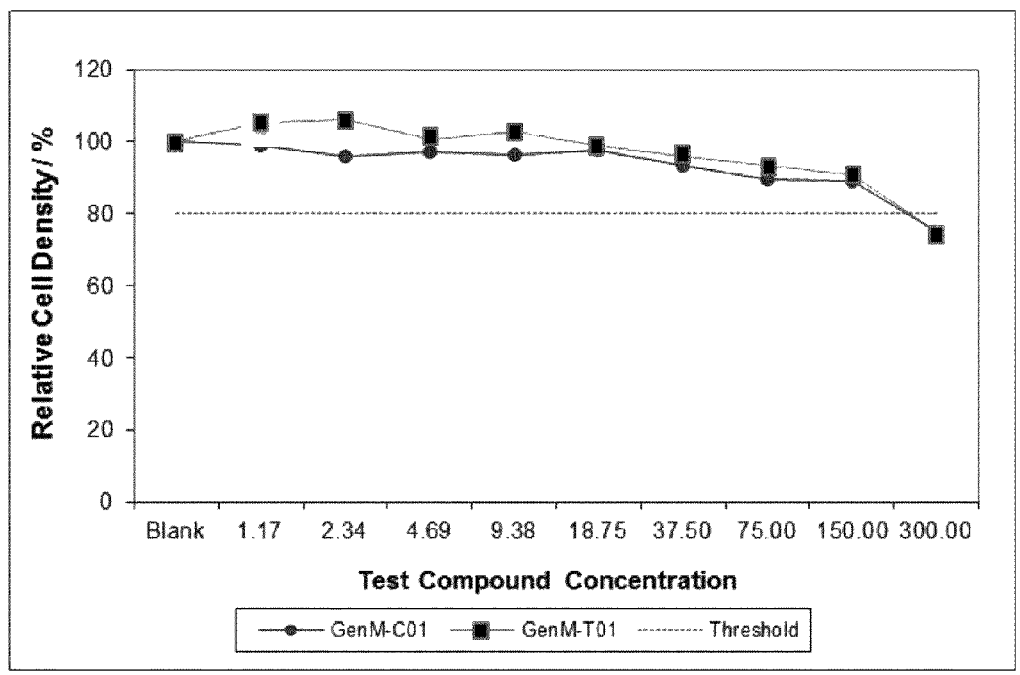

This application is a national stage filing under 35 U.S.C. 371 of PCT/EP2014/069088 filed Sep. 8, 2014, which International Application was published by the International Bureau in English on Mar. 12, 2015, and application claims priority from European Application No. 13183519.1, filed Sep. 9, 2013, and European Application No. 14151979.3, filed on Jan. 21, 2014, which applications are hereby incorporated in their entirety by reference in this application.

FIELD OF THE INVENTION

The present invention relates to peptidyl nitril compounds and their use as inhibitors of dipeptidyl peptidase I, pharmaceutical compositions containing the same, and methods of using the same agents for treatment and/or prevention of inflammatory diseases in which dipeptidyl peptidase I is involved, especially inflammatory diseases mediated by mast cells and neutrophil cells, e.g. chronic obstructive pulmonary disease and other respiratory diseases.

BACKGROUND OF THE INVENTION

Dipeptidyl peptidase I (DPPI; EC 3.4.14.1) also known as cathepsin C is a lysosomal cysteine peptidase belonging to the papain family. The enzyme is constitutively expressed in many tissues with highest levels in lung, kidney, liver and spleen. The cDNAs encoding rat, human and murine DPPI have been cloned and sequenced and it has been shown that the enzyme is highly conserved. DPPI is synthesized as an inactive precursor (Zymogen), and is activated by a non-autocatalytic excision of an internal activation peptide within the N-terminal propeptide. DPPI is the only member of the papain family that is functional as a tetramer, consisting of four identical subunits. Each is composed of an N-terminal fragment (the residual propart), a heavy chain and a light chain. Once activated, DPPI catalyzes the removal of dipeptides from the N-terminal end of polypeptide substrates with broad specificity. The pH optimum lies in the region of pH 5-7 using human DPPI. Recent data suggests that, beside of being an important enzyme in lysosomal protein degradation, DPPI also functions as a key enzyme in the activation of granule serine peptidases in neutrophils (cathepsin G, proteinase 3, neutrophil serine protease 4 and elastase), mast cells (chymase and tryptase) and cytotoxic T lymphocytes and natural killer cells (granzymes A and B).

Mast cells are found in many tissues, but are present in greater numbers along the epithelial linings of the body, such as the skin, respiratory tract and gastrointestinal tract. Mast cells are also located in the perivascular tissue surrounding small blood vessels. In humans, two types of mast cells have been identified; the T-type, which expresses only tryptase, and the MC-type, which expresses both tryptase and chymase. In humans, the T-type mast cells are located primarily in alveolar tissue and intestinal mucose while the TC-type cells predominate in skin and conjuctiva. Mast cells can release a range of potent inflammatory mediators including cytokines, leukotrienes, prostaglandins, histamine and proteoglycans, but among the most abundant products of mast cell activation are the serine peptidases of the chymotrypsin family; tryptase and chymase. These peptidases are situated in the mast cell lysosomes as fully active enzymes. The exact site of tryptase and chymase activation from zymogen precursors is not known, but the Golgi apparatus might play a role in that regard. DPPI, which is particular abundant in mast cells, seems to be the key enzyme responsible for activation of chymase and tryptase. Moreover, tryptase and chymase are emerging as important mediators of allergic diseases such as asthma, inflammatory bowel disease and psoriasis. After secretion from activated mast cells, there is evidence that these peptidases are heavily involved in processes of inflammation, tissue remodelling, bronchoconstriction and mucus secretion, which have made these peptidases attractive for therapeutic intervention.

Neutrophils cause considerable damage in a number of pathological conditions. When activated, neutrophils secrete destructive granular enzymes including elastase and cathepsin G and undergo oxidative bursts to release reactive oxygen intermediates. Numerous studies have been conducted on each of these activating agents in isolation. Pulmonary emphysema, COPD, cystic fibrosis, sepsis and rheumatoid arthritis are just some examples of pathological conditions associated with the potent enzymes elastase and cathepsin G.

The strong evidence associating tryptase, chymase, elastase, cathepsin G and other similar inflammatory peptidases with inflammatory diseases, points out DPPI as an attractive target enzyme for therapeutic intervention against the above mentioned diseases and other similar inflammatory diseases, due to its central role in activating these peptidases (Adkison et al. 2002, J. Clin. Invest, 109, 363-271; Pham. et al. 2004, Immunol, 173,7277-7281).

WO2012130299 and WO2012119941 to PROZYMEX disclose nitrile compounds and use thereof as dipeptidyl peptidase inhibitors. WO 2009074829A1 to Astrazeneca also discloses peptidyl nitriles and use thereof as dipeptidyl peptidase inhibitors. WO 2010128324A1, WO154677A1 and WO 2010142985A1 to Astrazeneca discloses further nitrile compounds and use thereof as dipeptidyl peptidase inhibitors WO2013041497A1 to Boehringer Ingelheim International GMBH discloses nitrile compounds as dipeptidyl peptidase inhibitors. Nathalie Méethot, Daniel Guay, Joel Rubin, Diane Ethier, Karen Ortega, Simon Wong, Denis Normandin, Christian Beaulieu, T. Jagadeeswar Reddy, Denis Riendeau, and M. David Percival: In Vivo Inhibition of Serine protease Processing Requires a High Fractional Inhibition of Cathepsin C, Mol Pharmacol 73:1857-1865, 2008 disclose dipeptide nitrile cathepsin C inhibitors, Nathalie Méthot, Joel Rubin, Daniel Guay, Christian Beaulieu, Diane Ethier T. Jagadeeswar Reddy, Denis Riendeau, and M. David Percival: Inhibition of the Activation of Multiple Serine proteases with a Cathepsin C Inhibitor Requires Sustained Exposure to Prevent Pro-enzyme Processing J. Biol. Chem., Vol. 282, Issue 29, 20836-20846, Jul. 20, 2007 disclose dipeptide nitrile cathepsin C inhibitors. Jon Bondebjerg, Henrik Fuglsang, Kirsten Rosendal Valeur, John Pedersen and Lars Nærum, Dipeptidyl nitriles as human dipeptidyl peptidase I inhibitors, Bioorganic & Medicinal Chemistry Letters 16 (2006) 3614-3617 disclose compounds having a dipeptide nitrile scaffold as inhibitors of human dipeptidyl peptidase I.

OBJECT OF THE INVENTION

It is an object of the invention to provide novel compounds being inhibitors of dipeptidyl peptidase I, suitable for treatment of inflammatory diseases, cancers and infections. An additional object is that the compounds are potent in cell-based DPPI inhibition assays, and have good metabolic stability.

FIGURES

Figure 1B:
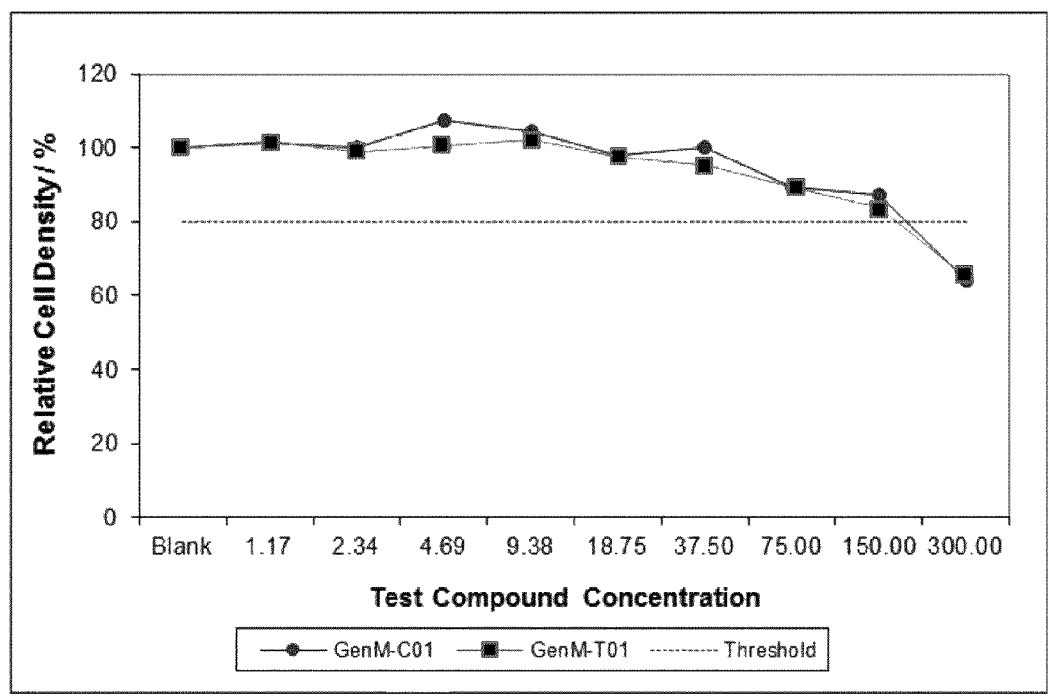

FIG. 1. Cytotoxicity results for compound PZ1025 analysed at the 24 hour timepoint (FIG. 1a.) and 48 hour timepoint (FIG. 1b.).

Figure 2A:
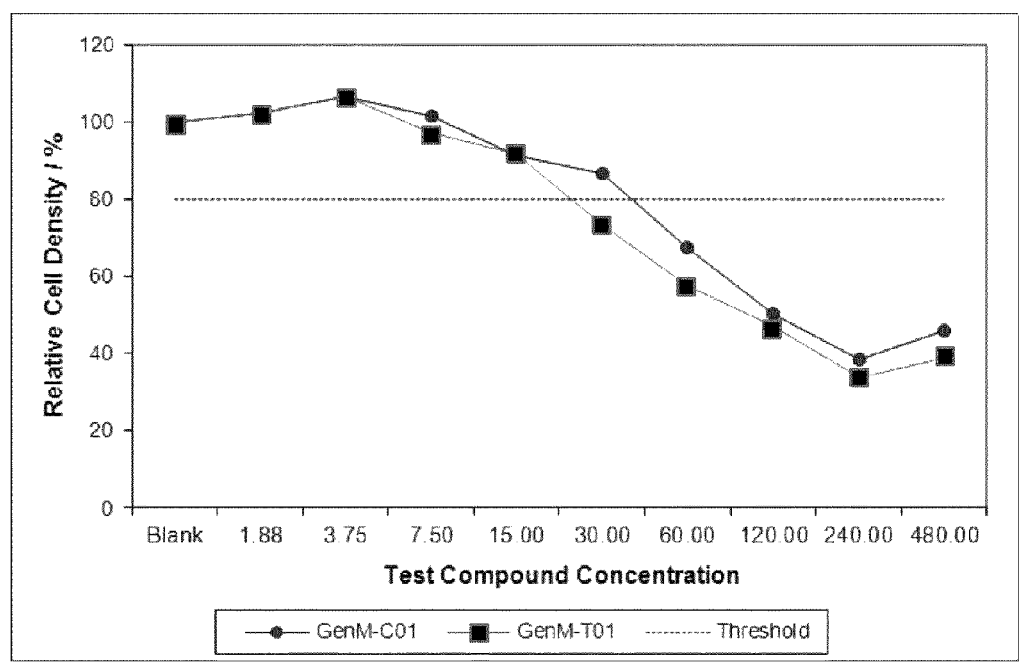
Figure 2B:
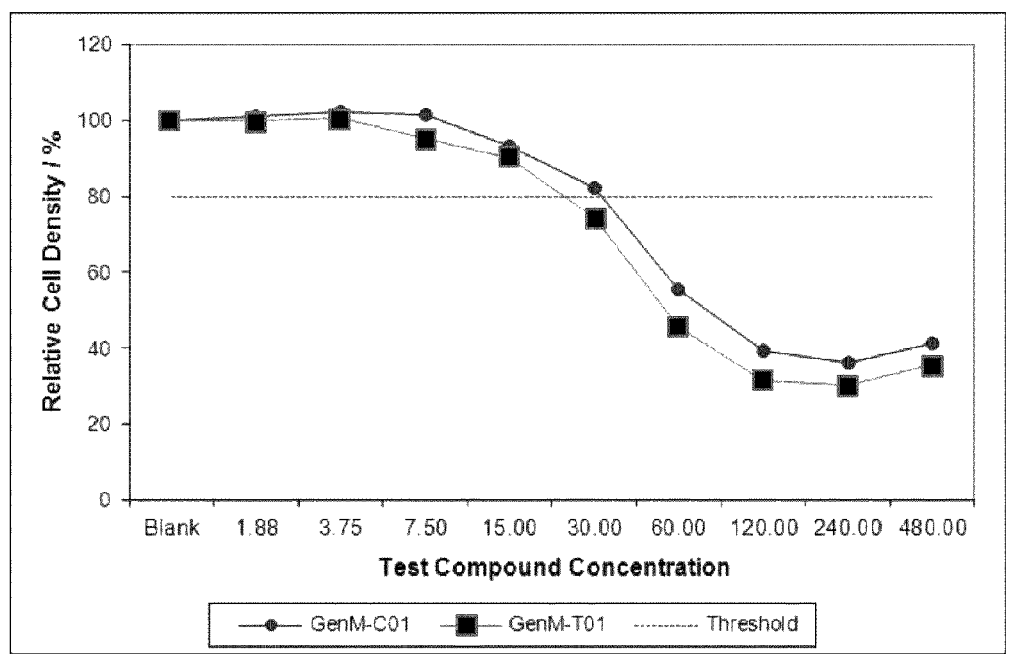

FIG. 2. Cytotoxicity results for compound PZ1024 analysed at the 24 hour timepoint (FIG. 2a.) and 48 hour timepoint (FIG. 2b.).

SUMMARY OF THE INVENTION

The present invention relates to a compound of the formula (I):

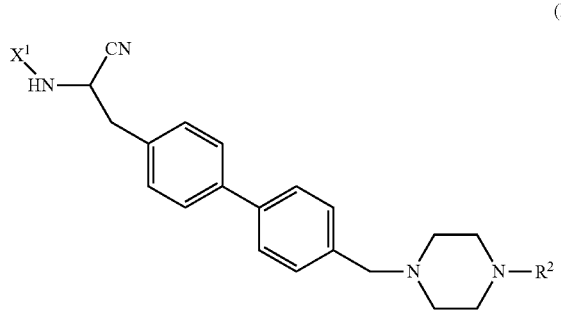

(I)

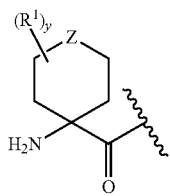

wherein $X^1$ represents wherein y represents 0, 1, 2, 3, 4, 5, 6, 7 or 8
wherein Z represents O (oxygen);
when y is 1 or 2, then $R^1$ independently represents deuterium; halogen; hydroxyl; cyano; oxo (=O); mercapto; or $C_{1-3}$-alkyl; which $C_{1-3}$-alkyl is optionally substituted with at least one substituent selected from halogen, hydroxyl, cyano and mercapto;
or when y represents 3, 4, 5, 6, 7 or 8, then $R^1$ represents deuterium;
wherein $R^2$ represents —$C_{3-6}$-cycloalkyl, —$C_{1-3}$-alkyl-$C_{3-6}$-cycloalkyl or —$C_{1-6}$-alkyl, which —$C_{1-6}$-alkyl is optionally substituted with at least one substituent selected from hydroxyl, cyano or amino; and pharmaceutically-acceptable salts, solvates and hydrates thereof.

$R^2$ may be —$C_{1-6}$-alkyl, which —$C_{1-6}$-alkyl is optionally substituted with at least one substituent selected from hydroxyl, cyano or amino. Suitably, $R^2$ is —$C_{1-6}$-alkyl, preferably —$C_{1-3}$-alkyl, more preferably methyl-, ethyl- or propyl-. Suitably, y=0 or 1, preferably 0. The following compound is of particular interest:

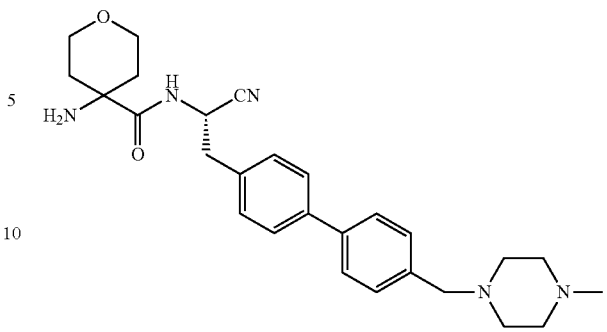

The term "DPPI" as used herein is intended to mean dipeptidyl peptidase I (EC 3.4.14.1) also known as cathepsin C, cathepsin J, dipeptidyl aminopeptidase I and dipeptidyl transferase. DPPI cleaves a dipeptide Xaa-Xbb from the N terminus of a polypeptide chain Xaa-Xbb-Xcc-[Xxx]$_n$, except when Xaa is Arg or Lys, or when Xbb or Xcc is Pro.

In the formulas, the group —CN is a nitrile group (—C≡N).

The wavy line in depicted substituents as e.g.

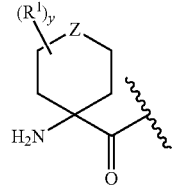

is used to indicate the bond, which is connected to the core molecule (formula I) as defined.

In the context of the present specification, unless otherwise stated, an alkyl substituent group or an alkyl moiety in a substituent group may be linear or branched.

The term "treatment" is defined as the management and care of a patient for the purpose of combating the disease, condition, or disorder and includes the administration of the compound of the present invention to prevent the onset of the symptoms or the complications, or alleviating the symptoms or the complications, or eliminating the disease, condition, or disorder.

"Half-life" (or "half-lives") refers to the time required for half of a quantity of a substance to be converted to another chemically distinct specie in vitro or in vivo.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

The compounds according to Formula (I) contain one or more asymmetric centers (also referred to as a chiral center) and may, therefore, exist as individual enantiomers, diastereomers, or other stereoisomeric forms, or as mixtures thereof. Chiral centers may also be present in a substituent such as an alkyl group. Where the stereochemistry of a chiral center present in Formula (I) or in any chemical structure illustrated herein, is not specified the structure is intended to encompass any stereoisomer and all mixtures thereof. Thus, compounds according to Formula (I)) containing one or more chiral center may be used as racemic mixtures, enantiomerically enriched mixtures, or as enantiomerically pure individual stereoisomers.

Individual stereoisomers of a compound according to Formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation. If there is a cycloalkyl group present, some substituent patterns may result in and axial or an equatorial configuration. Both forms are included, unless specified otherwise.

All tautomeric forms are also included in Formula (I), whether such tautorners exist in equilibrium or predominately in one form.

Preferred are the above compounds of formula (I), in their enantiomerically pure form of formula (II):

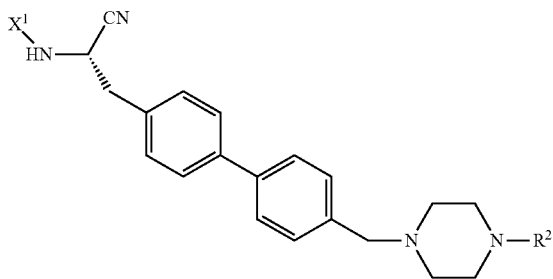

(II)

wherein $X^1$ and $R^2$ are as defined above.

The skilled artisan will appreciate that pharmaceutically-acceptable salts of the compounds according to Formula (I) may be prepared. Indeed, in certain embodiments of the invention, pharmaceutically-acceptable salts of the compounds according to Formula (I) may be preferred over the non-salt form because such salts impart greater stability or solubility to the molecule thereby facilitating formulation into a dosage form. Accordingly, the invention is further directed to pharmaceutically-acceptable salts of the compounds according to Formula (I).

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, funnaric acid, galacaric acid, gentisic acid, D-glucoheptonic acid, D-gluconic acid, D-glucuronic acid, glutamic acid, glutantic acid, glutaric acid, 2-oxo-glutaric acid, glycerophosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically-acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In the solid state, the compound of the invention can exist in crystalline, semi-crystalline and amorphous forms, as well as mixtures thereof. The skilled artisan will appreciate that pharmaceutically-acceptable solvates of the compound of the invention may be formed wherein solvent molecules are incorporated into the solid-state structure during crystallization. Solvates may involve water or non-aqueous solvents, or mixtures thereof. In addition, the solvent content of such solvates can vary in response to environment and upon storage. For example, water may displace another solvent over time depending on relative humidity and temperature. Solvates wherein water is the solvent that is incorporated into the solid-state structure are typically referred to as "hydrates." Solvates wherein more than one solvent is incorporated into the solid-state structure are typically referred to as "mixed solvates". Solvates include "stoichiometric solvates" as well as compositions containing variable amounts of solvent (referred to as "non-stoichiometric solvates"). Stoichiometric solvates wherein water is the solvent that is incorporated into the solid-state structure are typically referred to as "stoichiometric hydrates", and non-stoichiometric solvates wherein water is the solvent that is incorporated into the solid-state structure are typically referred to as "non-stoichiometric hydrates". The invention includes both stoichiometric and non-stoichiometric solvates.

In addition, crystalline forms of the compounds of the invention, including solvates thereof, may contain solvent molecules, which are not incorporated into the solid-state structure. For example, solvent molecules may become trapped in the crystals upon isolation. In addition, solvent molecules may be retained on the surface of the crystals. The invention includes such forms.

The compound of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, optic, intravaginal, and intranasal administration.

The compound of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for the compound of the invention depend on the pharmacokinetic properties of that compound, such as absorption, distribution, and half-life, which can be determined by the skilled artisan. In addition, suitable dosing regimens, including the amount administered and the duration such regimens are administered, for the compound of the invention depend on the condition being treated, the severity of the condition being treated, the age and physical condition of the patient being treated, the medical history of the patient to be treated, the nature of concurrent therapy, the particular route of administration chosen, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Typical daily dosages range from 1 mg to 1000 mg.

The compound of the invention may be administered as a prodrug. As used herein, a "prodrug" of the compound of the invention is a functional derivative of the compound which, upon administration to a patient, eventually liberates the compound of the invention in vivo. Administration of the compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In both drug discovery and drug development, prodrugs have become an established tool for improving physicochemical, biopharmaceutical or pharmacokinetic properties of pharmacologically active agents that overcome barriers to a drug's usefulness.

Coupling of short peptides or single amino acids as carriers of a therapeutic agent can be used as an effective type of prodrug approach. In this approach an amino acid or a di- (or oligo)peptide moiety is linked to a free (primary or secondary) amino group of the drug through an amide bond, that can be specifically cleaved by an endogenous peptidase, e.g. dipeptidyl peptidase IV (DPPIV/CD26), dipeptidyl peptidase I (DPPI/cathepsin C), aminopeptidase N (APN/CD13), pyroglutamyl aminopeptidase, proline iminopeptidase, aminopeptidase P, elastase, cathepsin G, proteinase 3, tryptase or chymase.

The amino acid or a di- or oligo-peptide moiety can consist of proteinogenic amino acids (i.e. amino acids that occur naturally in proteins) or non-proteinogenic amino acids (i.e. non-proteinogenic amino acids that either occur naturally or are chemically synthesized).

In one aspect, the compound disclosed herein is linked via a free (primary or secondary) amino group to an amino acid or a di- (or oligo)peptide moiety. These prodrugs may be converted to the desired active compound by a peptidase catalyzed reaction.

The compounds of general formula I may be used on their own or combined with other active substances of formula I according to the invention. The compounds of general formula I may optionally also be combined with other pharmacologically active substances. These include, B2-adrenoceptor-agonists (short and long-acting), anti-cholinergics (short and long-acting), anti-inflammatory steroids (oral and topical corticosteroids), cromoglycate, nnethylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRLI modulators, LTB4-receptor (BLTI, BLT2) antagonists, Histamine HI receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, J K1, J K2, J K3 or SAP, inhibitors of the NF-κB signalling pathway as for example IKK2 kinase inhibitors, iNOS inhibitors, MRP4 inhibitors or leukotriene biosynthese inhibitors.

The compounds disclosed herein will normally, but not necessarily, be formulated into a pharmaceutical composition prior to administration to a patient. Accordingly, in another aspect a pharmaceutical composition comprising, as an active substance, the compound as disclosed herein or a pharmaceutically acceptable salt thereof together with a pharmaceutically acceptable adjuvant, carrier or diluent, is provided.

The pharmaceutical compositions disclosed herein may be prepared and packaged in bulk form wherein a safe and effective amount of the compound disclosed herein can be extracted and then given to the patient such as with powders, syrups, and solutions for injection. Alternatively, the pharmaceutical compositions disclosed herein may be prepared and packaged in unit dosage form wherein each physically discrete unit contains a safe and effective amount of the compound as disclosed herein. When prepared in unit dosage form, the pharmaceutical compositions disclosed herein typically contain from 1 mg to 1000 mg.

The pharmaceutical compositions disclosed herein typically contain one compound as disclosed herein. However, in certain embodiments, the pharmaceutical compositions of the invention may optionally further comprise one or more additional pharmaceutically active compounds. Conversely, the pharmaceutical compositions of the invention typically contain more than one pharmaceutically-acceptable excipient. However, in certain embodiments, the pharmaceutical compositions of the invention contain one pharmaceutically-acceptable excipient.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable. The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company). In one aspect, the invention is directed to a solid oral dosage form such as a tablet or capsule comprising a safe and effective amount of the compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc. In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise the compound of the invention as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides.

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation. Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape.

Aerosols may be formed by suspending or dissolving the compound of the invention in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising the compound of the invention will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Suspensions and solutions comprising the compound of the invention may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of the invention may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compounds according to Formula I are prepared using conventional organic syntheses. Suitable synthetic routes are depicted below in the following general reaction schemes. Starting materials and reagents depicted below in the general reaction schemes are commercially available or can be made from commercially available starting materials using methods known by those skilled in the art.

The compounds disclosed herein may be converted to a pharmaceutically acceptable salt thereof, preferably an acid addition salt such as a hydrochloride, hydro bromide, trifluoroacetate, sulphate, phosphate, acetate, fumarate, maleate, tartrate, lactate, citrate, pyruvate, succinate, oxalate, methane sulphonate or p-toluenesulphonate. The compound of formula (1) and pharmaceutically acceptable salts thereof may exist in solvated, for example hydrated, as well as unsolvated forms, and the present invention encompasses all such solvated forms. In a further aspect, the compound disclosed herein is in the form of a pharmaceutically acceptable salt thereof.

In a further aspect, the compounds disclosed herein are for use in medicine such as for use as a dipeptidyl peptidase I (DPPI) inhibitor. In one aspect, they have activity as pharmaceuticals, in particular as inhibitors of dipeptidyl peptidase I activity, and thus may be used in the treatment of:

Obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); acute lung injury; acute respiratory distress syndrome; bronchitis, including infectious and eosinophilic bronchitis; emphysema; bronchiectasis; cystic fibrosis; alpha-1 antitrypsin deficiency; sarcoidosis; farmer's lung and related diseases; hypersensitivity pneumonitis; lung fibrosis, including cryptogenic fibrosing alveolitis, idiopathic interstitial pneumonias, fibrosis complicating antineoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; psoriasis, atopic dermatitis, contact dermatitis or other eczematous dermatoses, and delayed-type hypersensitivity reactions; phyto- and photodermatitis; seborrhoeic dermatitis; dermatitis herpetiformis, lichen planus; lichen sclerosus et atrophica; pyoderma gangrenosum; skin sarcoid; discoid lupus erythematosus; pemphigus; pemphigoid; epidermolysis bullosa; urticaria; angioedema; vasculitides; toxic erythemas; cutaneous eosinophilias; alopecia areata; male-pattern baldness; Sweet's syndrome; Weber-Christian syndrome; erythema multiforme; cellulitis, both infective and non-infective; panniculitis; cutaneous lymphomas, non-melanoma skin cancer and other dysplastic lesions; drug-induced disorders including fixed drug eruptions; blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial; sepsis; nephritis including interstitial and glomerulonephritis; nephritic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female); acute and chronic implications following, for example, transplantation of kidney, heart, liver, lung, bone marrow, skin or cornea or following blood transfusion; or chronic graft versus host disease; rheumatoid arthritis; irritable bowel syndrome; inflammatory bowel disease; gout; pseudogout; Alzheimer's disease; systemic lupus erythematosus; multiple sclerosis; Hashimoto's thyroiditis; Graves' disease; Addison's disease; diabetes mellitus, including type-1 diabetes mellitus; idiopathic thrombocytopaenic purpura; eosinophilic fasciitis; hyper-1gE syndrome; antiphospholipid syndrome and Sazary syndrome; cancers with neutrophil involvement; treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; virus diseases such as genital warts, common warts, plantar warts, hepatitis B, hepatitis C, herpes simplex virus, molluscum contagiosum, variola, human immunodeficiency virus (H1V), human papilloma virus (HPV), cytomegalovirus (CMV), varicella zoster virus (VZV), rhinovirus, adenovirus, coronavirus, influenza, para-influenza; bacterial diseases such as tuberculosis and mycobacterium avium, leprosy; other infectious diseases, such as malaria, fungal diseases, chlamydia, candida, aspergillus, cryptococcal meningitis, pneumocystis camll, cryptosporidiosis, histoplasmosis, toxoplasmosis, trypanosome infection and leishmaniasis; congestive heart failure; atherosclerosis; coronary artery disease; myocardial infarction; reperfusion injury; abdominal aortic aneurysms (AAA); diabetic cardiomyopathy (DCM); hypertension; peripheral artery disease; cardiac arrhythmia; stroke and cardiomegaly.

In a further aspect, the compounds disclosed herein are for use as a dipeptidyl peptidase I inhibitor.

In a further aspect, the compounds or pharmaceutical compositions disclosed herein are for use in treating asthma, chronic obstructive pulmonary disease, bronchiectasis, cystic fibrosis, alpha-1 antitrypsin deficiency, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis.

In a further aspect, the compounds or pharmaceutical compositions disclosed herein are for use in treating asthma, chronic obstructive pulmonary disease, bronchiectasis, cystic fibrosis, alpha-1 antitrypsin deficiency, acute lung injury; acute respiratory distress syndrome, congestive heart failure, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis or sepsis.

In yet a further aspect, the compounds or pharmaceutical compositions disclosed herein are for use in treating asthma, chronic obstructive pulmonary disease, bronchiectasis, cystic fibrosis, alpha-1 antitrypsin deficiency, congestive heart failure, myocardial infarction, reperfusion injury, abdominal aortic aneurysms, diabetic cardiomyopathy, gout, pseudogout, respiratory syncytial virus infection, rheumatoid arthritis or sepsis.

For the above-mentioned therapeutic uses the dosage administered will, of course, vary with the compound employed, the mode of administration, the treatment desired and the disorder indicated.

In a further aspect, the pharmaceutical composition in unit dosage form, comprises from about 1 µg to about 1000 mg such as, e.g., from about 10 µg to about 500 mg, from about 0.05 to about 100 mg or from about 0.1 to about 50 mg, of the active substance.

In yet a further aspect, disclosed herein is a compound which 24 hours after a single subcutaneous animal dosing at a concentration of 10 µmol/kg, has a concentration in bone marrow of 250 nM or more, such as 500 nM or, 750 nM or more or 1000 nM or more.

In yet a further aspect, disclosed herein is a compound which 12 hours after a single subcutaneous animal dosing at a concentration of 10 µmol/kg, has a concentration in bone marrow of 1000 nM or more, such as 1500 nM or more, 2000 nM or more, 3000 nM or more, or 5000 nM or more.

In a further aspect, the pharmaceutical composition disclosed herein is for oral, nasal, transdermal, pulmonal or parenteral administration.

In one aspect, a method of treating an obstructive airways disease in a patient suffering from, or at risk of, said disease, which comprises administering to the patient a therapeutically effective amount of the compound of formula (I) or a pharmaceutically acceptable salt thereof, is provided herein.

In one aspect, a method for the treatment of ailments, the method comprising administering to a subject in need thereof an effective amount of the compound as disclosed herein or of a composition as disclosed herein, is provided.

In a further aspect, an effective amount of the compound as disclosed herein is in a range of from about 1 µg to about 1000 mg such as, e.g., from about 10 µg to about 500 mg, from about 0.05 to about 100 mg or from about 0.1 to about 50 mg per day.

In one aspect, the use of the compound or pharmaceutical composition as disclosed herein for the preparation of a medicament, is provided.

In one aspect, the use of the compound, a pharmaceutically acceptable salt thereof or pharmaceutical composition as disclosed herein for the preparation of a medicament for treating asthma, chronic obstructive pulmonary disease, bronchiectasis, cystic fibrosis, alpha-1 antitrypsin deficiency, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis, is provided.

In one aspect, the use of the compound, a pharmaceutically acceptable salt thereof or pharmaceutical composition as disclosed herein in the manufacture of a medicament for treating asthma, chronic obstructive pulmonary disease, bronchiectasis, cystic fibrosis, alpha-1 antitrypsin deficiency, acute lung injury, acute respiratory distress syndrome, congestive heart failure, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis or sepsis, is provided.

In one aspect, the use of the compound, a pharmaceutically acceptable salt thereof or pharmaceutical composition as disclosed herein in the manufacture of a medicament for treating asthma, chronic obstructive pulmonary disease, bronchiectasis, cystic fibrosis, alpha-1 antitrypsin deficiency, congestive heart failure, myocardial infarction, reperfusion injury, abdominal aortic aneurysms, diabetic cardiomyopathy, gout, pseudogout, respiratory syncytial virus infection, rheumatoid arthritis or sepsis is provided.

In one aspect, a method for modulating DPPI levels in a subject in need thereof comprising administering to said subject an amount of the compound or a pharmaceutically acceptable salt thereof as disclosed herein or a composition as disclosed herein in an amount effective to modulate said DPPI levels in said subject, is provided.

In one aspect, said DPPI is inhibited.

In one aspect, a combination of the compound or a pharmaceutically acceptable salt thereof as disclosed herein and one or more agents independently selected from: a non-steroidal glucocorticoid receptor agonist; a selective β2 adrenoceptor agonist; a phosphodiesterase inhibitor; a peptidase inhibitor; a glucocorticoid; an anticholinergic agent; a modulator of chemokine receptor function; and an inhibitor of kinase function, is provided.

In another aspect, a method for treatment of a medical condition selected from the group selected from asthma, chronic obstructive pulmonary disease, bronchiectasis, cystic fibrosis, alpha-1 antitrypsin deficiency, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis, is provided, said method comprising administration of a pharmaceutically effective amount of a compound of formula (I) or the composition according to the invention. Suitably, in this method, the medical condition is selected from the group selected from asthma, chronic obstructive pulmonary disease, bronchiectasis, cystic fibrosis, alpha-1 antitrypsin deficiency, congestive heart failure, myocardial infarction, reperfusion injury, abdominal aortic aneurysms, diabetic cardiomyopathy, gout, pseudogout, respiratory syncytial virus infection, rheumatoid arthritis or sepsis.

The invention relates to the following numbered aspects:

Aspect 1: A compound of the formula (I)

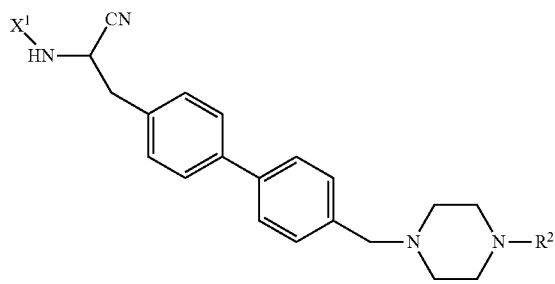

(I)

wherein $X^1$ represents

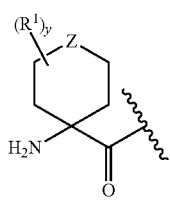

wherein y represents 0, 1, 2, 3, 4, 5, 6, 7 or 8;
wherein Z represents O (oxygen);

when y is 1 or 2, then $R^1$ independently represents deuterium; halogen; hydroxyl; cyano; oxo (=O); mercapto; or $C_{1-3}$-alkyl; which $C_{1-3}$-alkyl is optionally substituted with at least one substituent selected from halogen, hydroxyl, cyano and mercapto;

or when y represents 3, 4, 5, 6, 7 or 8, then $R^1$ represents deuterium;

wherein $R^2$ represents —$C_{3-6}$-cycloalkyl, —$C_{1-3}$-alkyl-$C_{3-6}$-cycloalkyl or —$C_{1-6}$-alkyl, which —$C_{1-6}$-alkyl is optionally substituted with at least one substituent selected from hydroxyl, cyano or amino as well as pharmaceutically-acceptable salts, solvates and hydrates thereof.

Aspect 2: The compound according to aspect 1, wherein $R^2$ is —$C_{1-6}$-alkyl, which —$C_{1-6}$-alkyl is optionally substituted with at least one substituent selected from hydroxyl, cyano or amino.

Aspect 3: The compound according to any one of the preceding aspects, wherein $R^2$ is —$C_{1-6}$-alkyl, preferably —$C_{1-3}$-alkyl, more preferably methyl-, ethyl- or propyl-.

Aspect 4: The compound according to any one of the preceding aspects, wherein y=0 or 1, preferably 0.

Aspect 5: The compound according to any one of the preceding aspects, being:

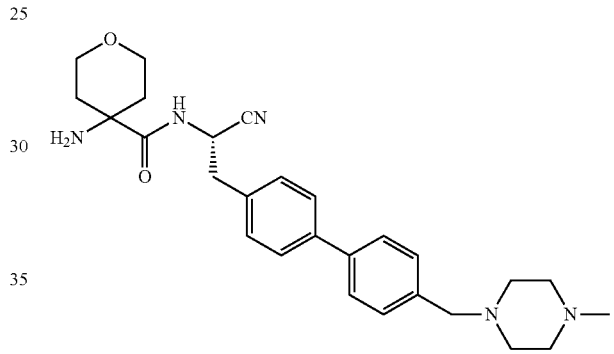

Aspect 6: The compound according to any one of the preceding aspects, in the enantiomerically pure form of formula (II):

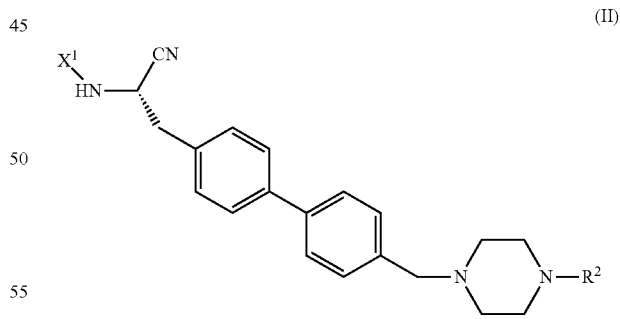

(II)

wherein $X^1$ and $R^2$ are as defined in any one of the preceding aspects.

Aspect 7: A pharmaceutical composition comprising a compound of the formula (I) according to any one of aspects 1-6, or a pharmaceutically acceptable salt thereof, together with at least one pharmaceutically-acceptable adjuvant, carrier or diluent.

Aspect 8: The compound according to any one of aspects 1-6 or composition according to aspect 7 for use as a medicament.

Aspect 9: A compound according to any one of aspects 1-6 or composition according to aspect 7 for treating asthma, chronic obstructive pulmonary disease, bronchiectasis, cystic fibrosis, alpha-1 antitrypsin deficiency, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis.

Aspect 10: A compound according to any one of aspects 1-6 or composition according to aspect 7 for treating asthma, chronic obstructive pulmonary disease, bronchiectasis, cystic fibrosis, alpha-1 antitrypsin deficiency, congestive heart failure, myocardial infarction, reperfusion injury, abdominal aortic aneurysms, diabetic cardiomyopathy, gout, pseudogout, respiratory syncytial virus infection, rheumatoid arthritis or sepsis.

Aspect 12: A method for treatment of a medical condition selected from the group selected from asthma, chronic obstructive pulmonary disease, bronchiectasis, cystic fibrosis, alpha-1 antitrypsin deficiency, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis, said method comprising administration of a pharmaceutically effective amount of a compound of formula (I) according to any one of aspects 1-6 or composition according to aspect 7.

Aspect 12: The method according to aspect 11, wherein the medical condition is selected from the group selected from asthma, chronic obstructive pulmonary disease, bronchiectasis, cystic fibrosis, alpha-1 antitrypsin deficiency, congestive heart failure, myocardial infarction, reperfusion injury, abdominal aortic aneurysms, diabetic cardiomyopathy, gout, pseudogout, respiratory syncytial virus infection, rheumatoid arthritis or sepsis.

Aspect 13: Use of a compound of formula (I) according to any one of aspects 1-6 or composition according to aspect 7 for the manufacture of a medicament for the treatment of asthma, chronic obstructive pulmonary disease, bronchiectasis, cystic fibrosis, alpha-1 antitrypsin deficiency, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis.

Aspect 14: Use according to aspect 13, wherein the medicament is for the treatment of asthma, chronic obstructive pulmonary disease, bronchiectasis, cystic fibrosis, alpha-1 antitrypsin deficiency, congestive heart failure, myocardial infarction, reperfusion injury, abdominal aortic aneurysms, diabetic cardiomyopathy, gout, pseudogout, respiratory syncytial virus infection, rheumatoid arthritis or sepsis.

MATERIALS AND METHODS

Cell Based DPPI Inhibition Assay

The herein described compounds are DPPI inhibitors, which indirectly inhibit the activity of serine peptidases that are activated by DPPI, such as elastase. Using the cell based assay described below, the biological activity of the compounds of the invention or other DPPI inhibitors may be determined.

Neutrophil elastase enzymatic activities in U937 cells grown in the presence of DPPI inhibitors were measured by methods modified from Méthot N; Rubin J; Guay D; Beaulieu C; Ethier D; Reddy T J; Riendeau D and Percival M D (2007) 3 Biol Chem, 282, 20836-20846. U937 cells were propagated in culture media (RPMI 1640, supplemented with 10% FBS, 10 mM Hepes, 1 mM sodium pyrovate, 100 units/ml of each of penicillin and streptomycin). Cells were seeded in 12-well plates at $0.4 \times 10^6$ cells/ml in volumes of 1.5 ml per well in the presence of no or increasing concentrations of DPPI inhibitor. 12 points in duplicate in the range of 0.1 nM to 50 µM inhibitor were tested. After 24 hours cells were harvested, washed with PBS and lysed in 20 mM Tris-HCl, pH 7.5, 100 mM NaCl, 0.2% Triton X-100. Debris was removed by centrifugation and supernatants were retained. The extracts were mixed with assay buffer (50 mM Tris, 0.1% Triton X-100, 0.5 M NaCl, pH 8.0) supplemented with substrate (MetOSuc-Ala-Ala-Pro-Val-pNA; Bachem; Cat. No. L-1335) to a final concentration of 0.9 mM.

The activity of neutrophil elastase was determined by measuring the enzymatic release of chromogenic p-nitroaniline from the substrate MetOSuc-Ala-Ala-Pro-Val-pNA, which leads to an increase in absorbance at 405 nm. Assays were carried out in 96-well plates in a final volume of 200 µL at 37° C., and absorbance was measured 8 times during 21-35 minutes using a plate reader. $IC_{50}$ was determined using a 4-parameter logistic equation in a non-linear curve fitting routine.

Human DPPI Inhibition Assay

Using this assay, the $IC_{50}$ value of the compound of the invention may be determined using Gly-Phe-paranitroanilide as a DPPI specific substrate.

Assay buffer: 20 mM citric acid (2.1 g citric acid), 150 mM NaCl (4.4 g NaCl) and 2 mM EDTA (370 mg EDTA) was dissolved in 500 mL $H_2O$, and pH was adjusted to 4.5 with HCl.

Substrate: Gly-Phe-paranitroanilide (Sigma Aldrich; Cat. No G0142) was used as the substrate for determination of $IC_{50}$ values. Km was 2.2 mM. The substrate was solubilized in dinnethylformamid to give a 0.2-0.5 M stock solution, which was then further diluted with stirring in assay buffer to a final concentration of 1 mM.

DPPI: Human DPPI (obtained from UNIZYME Laboratories A/S, DK-2970 Høsholm, Denmark) was stored at −20° C. in a buffer containing 2.5 mM Na-phosphate, 150 mM NaCl, 2 mM cysteamine, 50% glycerol, pH 7.0 at a concentration of 1-2 mg/mL (5-10 µM). This stock solution was diluted 500-1000 times in assay buffer to a concentration of 10-20 nM.

Assay conditions: The assay was performed in 96-well plates. Diluted enzyme (25 µL) was added to the well, followed by 25 µL of test substance in varying concentrations, and the solution was mixed. The plate was incubated at 37° C. for 5 minutes, followed by addition of 150 µL of 1 mM substrate prewarmed to 37° C. (corresponding to a substrate concentration of 750 µM in the assay). The absorption was measured at 405 nm at 37° C. for every 90 seconds for 12 minutes or every 20 seconds for 4 minutes. Each measurement was made in duplicate. $IC_{50}$ was determined using a 4-parameter logistic equation in a non-linear curve fitting routine.

Test for Metabolic Stability

The test for metabolic stability was performed by Absorption System, Exton, Pa. 19341, USA.

The test compound (DPPI inhibitor) was dissolved in 100% DMSO at a concentration of 10 mM. The reaction mixture, consisted of Mouse or Human Liver Microsomes (1.0 mg/mL), 1 mM NADPH, 100 nnM Potassium Phosphate, pH 7.4, 10 mM Magnesium Chloride and test compound at a concentration of 5 µM.

An aliquot of the reaction mixture (without cofactors) was incubated in a shaking water bath at 37° C. for 3 minutes. Another aliquot of the reaction mixture was prepared as the negative control. The test compound was added into both the reaction mixture and the negative control at a final concentration of 5 µM.

The reaction was initiated by the addition of NADPH to 1 mM (not into the negative controls) and then incubated in a shaking water bath at 37° C. Aliquots (100 µL) were withdrawn at 0, 10, 20, 30, and 60 minutes or at 0, 15, 30 and 60 minutes and combined with 900 µL of ice-cold 50/50 acetonitrile/dH$_2$O to terminate the reaction. A control (testosterone) was run simultaneously with the test compound in a separate reaction. LC/MS/MS is used to determine the peak area response ratio (peak area corresponding to test compound or control divided by that of an analytical internal standard). The natural log of the percent remaining was plotted versus time. A linear fit was used to determine the rate constant. The fit was truncated if the percent remaining of test compound was less than 10%. The elimination half-lives associated with the disappearance of the test and control compounds were determined to compare their relative metabolic stability.

Test for Inhibition of CYP2C9, CYP2D6 and CYP3A4 Enzymes

The test for inhibition of CYP2C9, CYP2D6 and CYP3A4 enzymes was performed by Absorption System, Exton, Pa. 19341, USA according to the procedure described below.

The IC$_{50}$ values of Example 1 of WO2012119941 (PZ1024) and the compound of the present invention (PZ1025) for CYP enzymes (CYP2C9, CYP2D6, and CYP3A4) in Human Liver Microsomes were measured. The test compounds, at eight concentration levels (0, 0.137, 0.412, 1.23, 3.70, 11.1, 33.3 and 100 µM), were incubated with pooled Human Liver Microsomes (0.25 mg protein/mL) at 37° C. in the presence of phosphate buffer (100 mM, pH 7.4), MgCl2 (5 mM), NADPH (1 mM), and CYP-specific probe substrate at approximately Km (6 µM diclofenac, 7 µM bufuralol and 75 µM testosterone for CYP2C9, CYP2D6, and CYP3A4, respectively). After a period of incubation, the samples were treated by the addition of protein precipitation solvent and centrifuged. CYP enzyme activities were measured by determining the formation of the CYP probe metabolites by LC-MS/MS, and the IC$_{50}$ (the concentration of an inhibitor causing 50% inhibition) was estimated using GraphPad Prism® software by fitting the experimental data (percent of control activity remaining at each concentration of test compound) to a sigmoidal model and non-linear regression analysis.

The CYP enzyme activities in the Human Liver Microsomes were verified in parallel by determining the inhibition of positive inhibitors on the CYP enzyme activities (sulfaphenazole, quinidine and ketoconazole for CYP2C9, CYP2D6, and CYP3A4, respectively). All CYP enzymes showed expected inhibitions by positive inhibitors, indicating that the human liver microsomes used in this study were metabolically active and responsive.

Test for Cytotoxicity

The test for cytotoxicity was performed by Cyprotex Discovery Ltd. 15 Beech lane, Macclesfield, Cheshire, SK10 2DR, UK.

Two strains of cultured human lymphoblastoid TK6 cells was used, GenM-T01 and GenM-C01. A dilution series of each test compound was generated in a 96-well, black microplate with an optically clear base. The plates was analysed at 24 hour and 48 hour time points using a microplate reader, that provides measurements of light absorbance for cells and solutions in the microplates wells.

Cytotoxicity was assessed using relative cell proliferation, quantified using optical absorbance. Cytotoxic compounds are those which reduce relative cell density below a significance threshold set at 80% compared to the vehicle-treated control, at one or more test concentrations.

EXAMPLE 1. (S)-4-amino-N-(1-cyano-2-(4'-((4-methylpiperazin-1-yl)methyl)biphenyl-4-yl)ethyl) tetrahydro-2H-pyran-4-carboxamide (PZ1025)

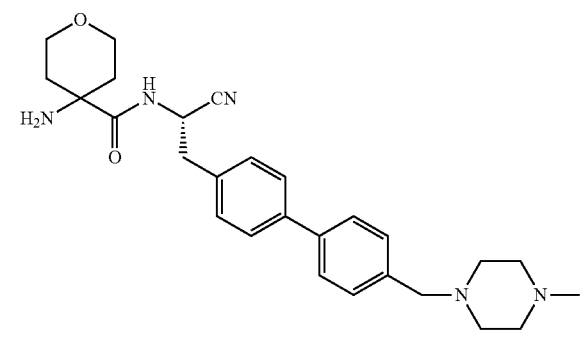 [SMILES: CN1CCN(Cc2ccc(-c3ccc(C[C@@H](C#N)NC(=O)C4(N)CCOCC4)cc3)cc2)CC1]

PZ1025

Synthetic scheme

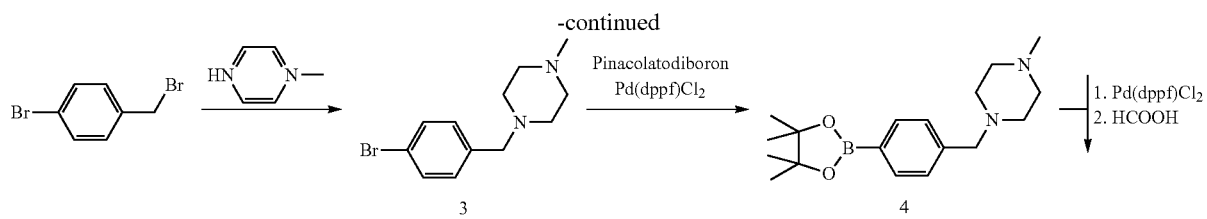

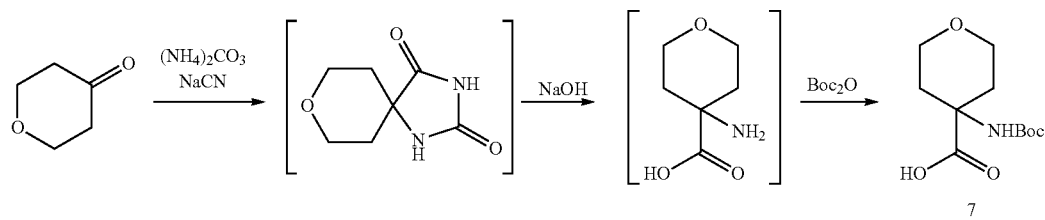

PROCEDURE

(S)-tert-Butyl 1-amino-3-(4-bromophenyl)-1-oxo-propan-2-ylcarbamate (1)

A solution of (S)-3-(4-bromophenyl)-2-(tert-butoxycarbonylamino)propanoic acid (20.0 g, 58.3 mol) in DCM (400 mL) was cooled in an ice-water bath and DMTMM (24.2 g, 87.5 mol) was added. The mixture was stirred at 0° C. for 1 h before addition of 25% $NH_3$—$H_2O$ (6 g, 87.5 mol). The reaction mixture was allowed to warm to room temperature and stirred for 12 h. The mixture was extracted with ethyl acetate three times and the combined organic layers were washed with brine, dried over anhydrous $Na_2SO_4$ and concentrated to afford compound 1 (19.0 g, yield 95%) as a white solid.

(S)-tert-Butyl 2-(4-bromophenyl)-1-cyanoethylcarbamate (2)

A solution of compound 1 (14.73 g, 43 mmol) in anhydrous pyridine (150 mL) was cooled in an ice-water batch and $POCl_3$ (8 mL, 77.4 mmol) was added dropwise over 30 min. The reaction mixture was stirred at 0° C. for 2 h and then allowed to warm to room temperature and stirred overnight. The mixture was treated with ice-water and extracted with ethyl acetate. The combined organic layers were washed with 1 M HCl solution, saturated aqueous $NaHCO_3$ and brine, respectively. The organic layer was dried over anhydrous $Na_2SO_4$ and concentrated. The residue was purified by flash column chromatography on silica gel (petroleum ether/EtOAc=50:1 to 10:1) to give compound 2 (9.67 g, yield 69.3%) as a white solid.

1-(4-Bromobenzyl)-4-methylpiperazine (3)

1-Methylpiperazine (37.4 g, 0.374 mol) was added dropwise to a mixture of 1-bromo-4-(bromomethyl)benzene (78.0 g, 0.312 mol) and $K_2CO_3$ (86.1 g, 0.624 mol) in DMF (400 mL) and the reaction mixture was stirred for 4 h at room temperature. The mixture was poured into water (1500 mL) and then extracted with EtOAc three times. The combined extracts were washed with brine, dried over anhydrous $Na_2SO_4$ and concentrated to give compound 3 (50.0 g, yield 59.5%) as a yellow oil.

Methyl-4-(4-(4,4,5,5-tetramethyl-1,3,2-dioxaborolan-2-yl)benzyl)piperazine (4)

To a stirred solution of compound 3 (35.0 g, 130 mmol) in 1,4-dioxane (500 mL) were added potassium acetate (38.3 g, 390 mmol) and pinacolatodiboron (33.0 g, 130 mmol). The mixture was evacuated and refilled with nitrogen (three times). Pd(dppf)Cl$_2$ (3.0 g, 1.3 mmol)

was added and the reaction mixture was stirred at 110° C. under nitrogen for 12 h. The mixture was cooled to room temperature and the solid was filtered off. The filtrate was concentrated and the residue was diluted with ethyl acetate and water. The organic layer was dried over anhydrous $Na_2SO_4$ and concentrated. The residue was purified by flash column chromatography on silica gel (DCM/MeOH=50:1 to 10:1) to give compound 4 (37.0 g, yield 90%) as a brown solid.

(S)-tert-Butyl 1-cyano-2-(4'-((4-methylpiperazin-1-yl)methyl)biphenyl-4-yl) ethyl carbamate (5)

To a stirred solution of compound 4 (5.0 g, 15.4 mmol) and compound 2 (4.4 g, 14.0 mmol) in 1,4-dioxane (200 mL) at room temperature was added sodium carbonate (3.7 g, 35 mmol). The mixture was evacuated and refilled with nitrogen (three times). Pd(dppf)Cl$_2$ (0.5 g, 0.22 mmol) was added and the reaction mixture was stirred at 90° C. under nitrogen for 12 h. The mixture was cooled to room temperature and the solid was filtered off. The filtrate was concentrated and the residue was diluted with ethyl acetate and water. The organic layer was dried over anhydrous $Na_2SO_4$ and concentrated. The residue was purified by flash column chromatography on silica gel (DCM/MeOH=50:1 to 10:1) to afford compound 5 (3.4 g, yield 50.7%) as a brown solid.

(S)-2-Amino-3-(4'-((4-methylpiperazin-1-yl)methyl)biphenyl-4-yl)propanenitrile (6)

Compound 5 (1.0 g, 2.3 mmol) was dissolved in 88% HCOOH (20 mL) and the reaction mixture was stirred at room temperature for 12 h. Saturated aqueous NaHCO$_3$ was added dropwise and the resulting mixture was extracted with DCM. The combined organic layers were washed with brine, dried over anhydrous $Na_2SO_4$ and concentrated. The residue was purified by flash column chromatography on silica gel (DCM/MeOH=100:1 to 20:1) to afford compound 6 (300 mg, yield 38%) as a white solid.

4-(tert-Butoxycarbonylamino)tetrahydro-2H-pyran-4-carboxylic acid (7)

To a suspension of dihydro-2H-pyran-4(3H)-one (5.0 g, 50 mmol) and (NH$_4$)$_2$CO$_3$ (24.5 g, 255 mmol) in ethanol/water (1:1, 100 mL) was added sodium cyanide (2.5 g, 51 mmol). The reaction mixture was heated at 50° C. for 12 h and than heated to 80° C. to decompose an excess of (NH$_4$)$_2$CO$_3$. Ethanol was removed and sodium hydroxide (8.16 g, 0.76 mmol) was added. The reaction mixture was refluxed overnight and then cooled to room temperature. The mixture was adjusted to pH=10 with 2 N HCl solution and Boc$_2$O (11.1 g, 51 mmol) and acetonitrile (50 mL) were added. The reaction mixture was stirred overnight at room temperature and ethyl acetate was added. The resulting mixture was adjusted to pH=3-4 with 2 N HCl solution carefully and the organic layer was separated and concentrated. The residue was purified by flash column chromatography on silica gel (DCM/MeOH=100:1) to afford compound 7 (3.0 g, yield 24% over three steps) as a white solid.

Boc-(S)-4-amino-N-(1-cyano-2-(4'-((4-methylpiperazin-1-yl) methyl) biphenyl-4-yl)ethyl)tetrahydro-2H-pyran-4-carboxamide (Boc-PZ1025)

To a solution of compound 6 (4.5 g, 13.51 mmol) in DCM (90 mL) in an ice-water bath was added DMTMM (7.5 g, 27 mmol). The mixture was stirred at 0° C. for 0.5 h and compound 7 (4-(tert-Butoxycarbonylamino)tetrahydro-2H-pyran-4-carboxylic acid; 4.0 g, 16.22 mmol) was added. The reaction mixture was allowed to warm to room temperature and stirred for 12 h. The mixture was extracted with EtOAc three times and the combined organic layers were washed with brine, dried over anhydrous $Na_2SO_4$ and concentrated. The residue was purified by flash column chromatography on silica gel (DCM/MeOH=20:1) to afford compound Boc-PZ1025 (6.3 g, yield 83.1%) as a light yellow solid.

(S)-4-amino-N-(1-cyano-2-(4'-((4-methylpiperazin-1-yl)methyl) biphenyl-4-yl)ethyl)tetrahydro-2H-pyran-4-carboxamide (PZ1025)

A solution of Boc-PZ1025 (8.5 g, 15.16 mmol) in 88% HCOOH (150 ml) was stirred for 3 h at room temperature. The mixture was poured into saturated aqueous NaOH (200 mL) and the resulting mixture was extracted with DCM twice. The organic layers were combined, washed with brine, dried over anhydrous $Na_2SO_4$ and concentrated. The residue was purified by flash column chromatography on silica gel (DCM/MeOH=40:1 to 20:1) to afford compound PZ1025 (3.9 g, 55.9% yield) as a white solid. $^1$H NMR (300 MHz, CDCl$_3$): δ8.25 (d, 1H, J=9.0 Hz), 7.61-7.53 (m, 4H), 7.42-7.33 (m, 4H), 5.14 (m, 1H), 3.95-3.85 (m, 2H), 3.67-3.62 (m, 2H), 3.60-3.57 (m, 2H), 3.16 (d, J=6.9 Hz, 2H), 2.56 (m, 8H), 2.35 (s, 3H), 2.32-2.18 (m, 2H), 1.33 (m, 1H), 1.21 (m, 1H); MS (ESI): m/z 446.4 [M+H]$^+$.

PZ1025 was found to have an IC$_{50}$ of 11 nM in the cell based DPPI inhibition assay and a half-life in human liver microsomes of more than 300 minutes. The combination of a good potency in a cell based DPPI inhibition assay and a good metabolic stability is particularly relevant in relation to achieve a pharmacological effect of a DPPI inhibitor during therapy in humans, as pharmacokinetic studies (see reference) have shown, that in vivo inhibition of elastase and cathepsin G require a high fractional and sustained level of DPPI inhibition, probably as high as 90% or more.

Reference. Méthot N, Quay D, Rubin J, Ethier D, Ortega K, Wong S, Normandin D, Beaulieu C, Reddy T J, Riendeau D, Percival M D. In vivo inhibition of serine protease processing requires a high fractional inhibition of cathepsin C. Mol Pharmacol. 2008 June; 73(6):1857-65.

COMPARATIVE EXAMPLES

Comparative Example A: Comparison with WO2012119941

Table 1 below compares PZ1025 (Example 1) and Example 1 of WO2012119941. The difference between Example 1 of WO2012119941 (PZ1024) and the compound of the present invention (PZ1025) is the oxygen in PZ1025 vs. the carbon in PZ1024. As shown in the table, the potency of PZ1025 and PZ1024 (Example 1 of WO2012119941) is nearly the same.

TABLE 1

| Structure | IC$_{50}$ nM | Metabolic stability human microsomes | Metabolic stability mouse microsomes | CYP inhibition IC$_{50}$ µM |
|---|---|---|---|---|
| 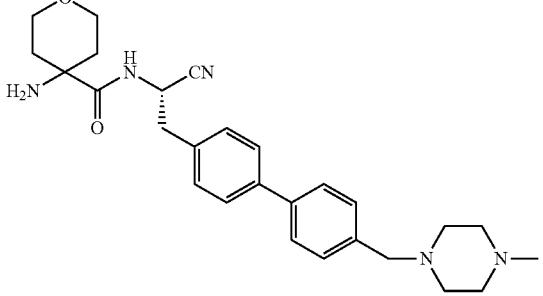 PZ1025 | 34 | t½ > 300 min | t½ ≈ 65 min | CYP2C9: >100<br>CYP2D6: >100<br>CYP3A4: >100 |
| 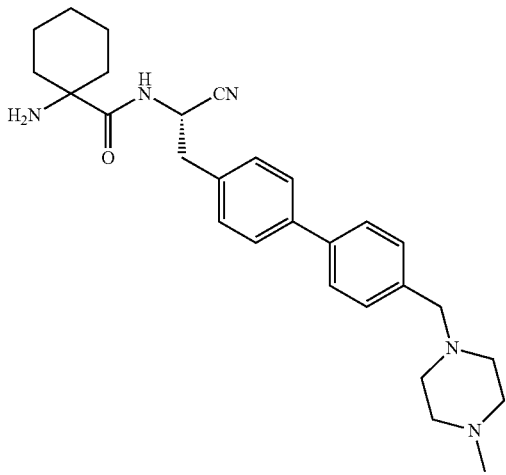 Example 1 of WO2012119941 (PZ1024) | 37 | t½ ≈ 55 min | t½ ≈ 10 min | CYP2C9: >100<br>CYP2D6: 18<br>CYP3A4: >100 |

Table 1 also shows the metabolic stability of PZ1025 and PZ1024 (Example 1 of WO2012119941) in human and mouse liver microsomes. The metabolic stability was determined as measured by the elimination half-lives (t½). The half-life of PZ1024 in human liver microsomes is ≈55 minutes, however the half-life of PZ1025 in human liver microsomes is more than 5 times higher (>300 minutes). The half-life of PZ1024 in mouse liver microsomes is ≈10 minutes, however the half-life of PZ1025 in mouse liver microsomes is more than 6 times higher (≈65 minutes).

The higher metabolic stability of PZ1025 (a compound of the present invention) is very beneficial, as the improved metabolic stability will increase the bioavailabity of PZ1025 as compared to the bioavailability of PZ1024. This is particularly relevant in relation to achieve a pharmacological effect of a DPPI inhibitor in both animal studies and during therapy in humans, as pharmacokinetic studies (see reference) have shown, that in vivo inhibition of elastase and cathepsin G require a high fractional and sustained level of DPPI inhibition, probably as high as 90% or more.

Table 1 also shows the selectivity of PZ1025 and PZ1024 (Example 1 of WO2012119941) with respect to CYP2C9, CYP2D6 and CYP3A4, which are some of the most important metabolizing CYP enzymes. Both PZ1025 and PZ1024 have a satisfactory selectivity (>100 µM) over CYP2C9 and CYP3A4, but only PZ1025 have a satisfactory selectivity (>100 µM) over CYP2D6.

Reference. Méthot N, Guay D, Rubin J, Ethier D, Ortega K, Wong S, Normandin D, Beaulieu C, Reddy T J, Riendeau D, Percival M D. In vivo inhibition of serine protease processing requires a high fractional inhibition of cathepsin C. Mol Pharmacol. 2008 June; 73(6):1857-65.

Comparative Example B: Comparison with WO2012119941

FIGS. 1 and 2 compare PZ1025 (Example 1) and Example 1 of WO2012119941 (PZ1024) with respect to cytotoxicity. FIG. 1 shows compound PZ1025 analysed at the 24 hour timepoint (FIG. 1a) and 48 hour timepoint (FIG. 1b.). FIG. 2 shows cytotoxicity results for compound PZ1024 analysed at the 24 hour timepoint (FIG. 2a.) and 48 hour timepoint (FIG. 2b.). Horizontal axis in each case is µM.

The highest concentration (µM) that does not cross the significance threshold is 150 µM for PZ1025 and 15 µM for PZ1024. It can therefore be concluded that PZ1025 is at least 5 times less toxic than PZ1024.

Comparative Example C: Comparison with WO2010128324

Table 2 below compares PZ1025 (Example 1) and Example 29 of WO2010128324. Example 29 of WO2010128324 (PZ1032) differs from the compound of the present invention (PZ1025) in the sulfonyl, instead of the methylene, bridging moiety between the phenyl and the piperazinyl ring (se structures in Table 2 below). As shown in Table 2, the potency of PZ1025 and PZ1032 measured in the cell based DPPI inhibition assay is essential the same.

and cathepsin G require a high fractional and sustained level of DPPI inhibition, probably as high as 90% or more.

REFERENCE

Méthot N, Guay D, Rubin J, Ethier D, Ortega K, Wong S, Normandin D, Beaulieu C, Reddy T J, Riendeau D, Percival M D. In vivo inhibition of serine protease processing requires a high fractional inhibition of cathepsin C. Mol Pharmacol. 2008 June; 73(6):1857-65.

TABLE 2

| Structure | Cell based DPPI inhibition assay $IC_{50}$ | Metabolic stability- Human MS | Metabolic stability Mouse MS |
|---|---|---|---|
| 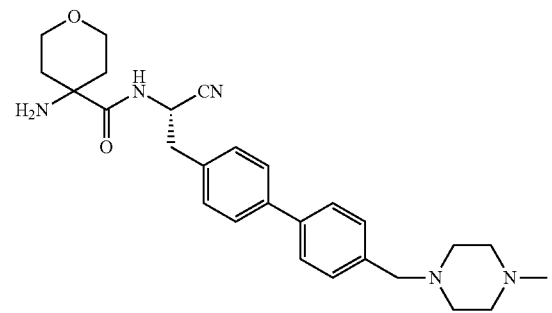 PZ1025 | ≈11 nM | $t\frac{1}{2}$ > 300 min | $t\frac{1}{2}$ ≈ 65 min |
| 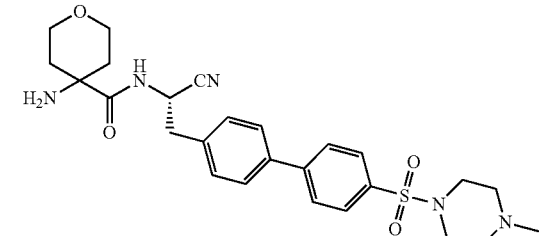 Example 29 of WO2010128324 (PZ1032) | ≈11 nM | $t\frac{1}{2}$ ≈ 50 min | $t\frac{1}{2}$ ≈ 35 min |

Table 2 also shows the metabolic stability of PZ1025 and PZ1032 (Example 29 of WO2010128324) in human and mouse liver microsomes (MS). The metabolic stability were determined as measured by the elimination Half-Lives ($t\frac{1}{2}$). The Half-Life of PZ1032 in human liver microsomes is 50 minutes, however the Half-Life of PZ1025 in human liver microsomes is more than 5 times higher (>300 minutes). The Half-Life of PZ1032 in mouse liver microsomes is 35 minutes, however the Half-Life of PZ1025 in mouse liver microsomes is about 2 times higher (≈65 minutes).

The higher metabolic stability of PZ1025 (a compound of the present invention) is very beneficial, as the improved metabolic stability will increase the bioavailabity of PZ1025 as compared to the bioavailability of PZ1032. This is particularly relevant when attempting to achieve a pharmacological effect of a DPPI inhibitor in both animal studies and during therapy in humans, as pharmacokinetic studies (see reference) have shown that in vivo inhibition of elastase

Comparative Example D: Structural Comparison with WO2012119941

The compounds of the present invention are inter alia characterized by a tetrahydro-pyranyl ring adjacent to the carboxamide moiety. WO 2012/119941 illustrates different structures comprising a bridged or fused oxygen-containing saturated ring system adjacent to the carboxamide moiety (cf. the fourth compound on page 57 and the fifth compound on page 58). No synthetic routes have been made available for these two compounds, and thus no biological tests have been carried out.

The tetrahydro-pyranyl ring represents a flexible structure known to adapt to various three-dimensional conformations. In contrast hereto, each of the two particular compounds of WO 2012/119941 represent structures wherein the bridging or fusing of the ring(s) hinder the conformational flexibility. This means that such bridged or fused oxygen-containing saturated ring systems have significantly different steric properties compared to a tetrahydro-pyranyl ring.

The invention claimed is:
1. A compound of the formula (I)

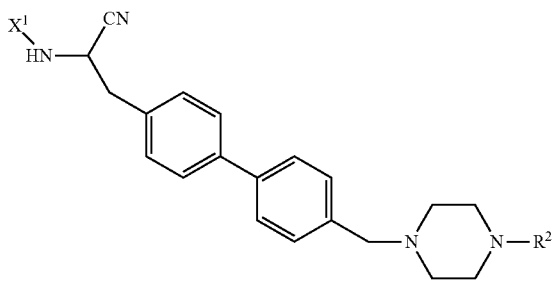

wherein X¹ represents

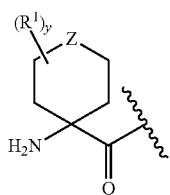

wherein y represents 0, 1, 2, 3, 4, 5, 6, 7 or 8;
wherein Z represents O (oxygen);
when y is 1 or 2, then R¹ independently represents deuterium; halogen; hydroxyl; cyano; oxo (=O); mercapto; or $C_{1-3}$-alkyl; which $C_{1-3}$-alkyl is optionally substituted with at least one substituent selected from halogen, hydroxyl, cyano and mercapto;
or when y represents 3, 4, 5, 6, 7 or 8, then R¹ represents deuterium;
wherein R² represents —$C_{3-6}$-cycloalkyl, —$C_{1-3}$-alkyl-$C_{3-6}$-cycloalkyl or —$C_{1-6}$-alkyl, which —$C_{1-6}$-alkyl is optionally substituted with at least one substituent selected from hydroxyl, cyano or amino; as well as pharmaceutically-acceptable salts thereof.
2. The compound according to claim 1 consisting of:

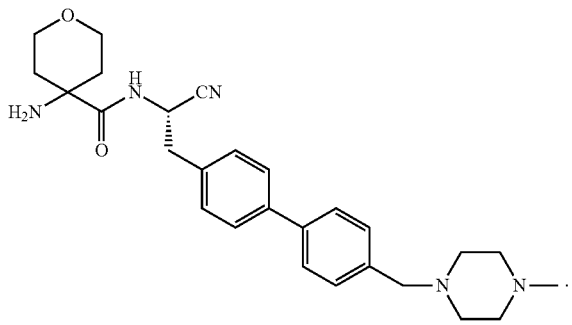 [SMILES: CN1CCN(Cc2ccc(-c3ccc(C[C@@H](C#N)NC(=O)C4(N)CCOCC4)cc3)cc2)CC1 ; "."]

3. The compound according to claim 1, wherein R² is —$C_{1-6}$-alkyl, which —$C_{1-6}$-alkyl is optionally substituted with at least one substituent selected from hydroxyl, cyano or amino.

4. The compound according to claim 1, wherein R² is —$C_{1-6}$-alkyl, preferably —$C_{1-3}$-alkyl, more preferably methyl-, ethyl- or propyl-.
5. The compound according to claim 1, wherein y represents 0, 1, 2, 3, or 4.
6. A pharmaceutical composition comprising a compound of the formula (I) according to claim 1, or a pharmaceutically acceptable salt thereof, together with at least one pharmaceutically-acceptable adjuvant, carrier or diluent.
7. A method for treatment of a medical condition selected from the group selected from asthma, chronic obstructive pulmonary disease, bronchiectasis, cystic fibrosis, alpha-1 antitrypsin deficiency, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis, said method comprising administering a pharmaceutically effective amount of a compound of formula (I) according to claim 1.
8. The method according to claim 7, wherein the medical condition is selected from the group selected from asthma, chronic obstructive pulmonary disease, bronchiectasis, cystic fibrosis, alpha-1 antitrypsin deficiency, congestive heart failure, myocardial infarction, reperfusion injury, abdominal aortic aneurysms, diabetic cardiomyopathy, gout, pseudogout, respiratory syncytial virus infection, rheumatoid arthritis or sepsis.
9. The compound according to claim 1, wherein y represents 0.
10. A pharmaceutical comprising a compound of the formula:

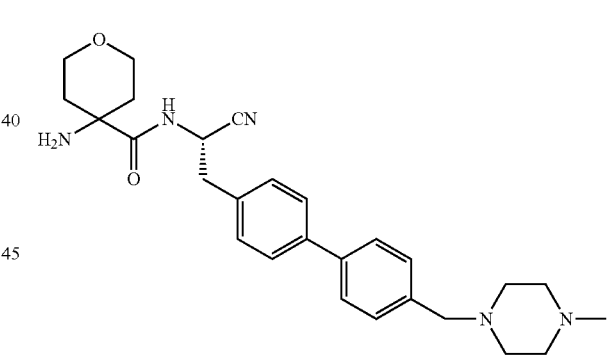

or a pharmaceutically acceptable salt thereof, together with at least one pharmaceutically-acceptable adjuvant, carrier or diluent.
11. The method of claim 7, wherein a symptom of said medical condition is alleviated.
12. The method of claim 8, wherein a symptom of said medical condition is alleviated.
13. A method for treatment of a medical condition selected from the group selected from asthma, chronic obstructive pulmonary disease, bronchiectasis, cystic fibrosis, alpha-1 antitrypsin deficiency, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis, said method comprising administering a pharmaceutically effective amount of a compound according to claim 2.

14. The method according to claim 11, wherein the medical condition is selected from the group selected from asthma, chronic obstructive pulmonary disease, bronchiectasis, cystic fibrosis, alpha-1 antitrypsin deficiency, congestive heart failure, myocardial infarction, reperfusion injury, abdominal aortic aneurysms, diabetic cardiomyopathy, gout, pseudogout, respiratory syncytial virus infection, rheumatoid arthritis or sepsis.

15. The method of claim 13, wherein a symptom of said medical condition is alleviated.

16. The method of claim 14, wherein a symptom of said medical condition is alleviated.

* * * * *